(12) United States Patent
Bask et al.

(10) Patent No.: US 10,449,386 B2
(45) Date of Patent: Oct. 22, 2019

(54) METHOD FOR OPTIMIZING A BRACHYTHERAPY RADIATION TREATMENT PLAN

(71) Applicant: Varian Medical Systems International AG, Cham (CH)

(72) Inventors: Joni Bask, Vantaa (FI); Toni Taiminen, Vantaa (FI)

(73) Assignee: Varian Medical Systems International AG, Steinhausen (CH)

(*) Notice: Subject to any disclaimer, the term of this patent is extended or adjusted under 35 U.S.C. 154(b) by 645 days.

(21) Appl. No.: 14/040,186

(22) Filed: Sep. 27, 2013

(65) Prior Publication Data

US 2014/0275713 A1 Sep. 18, 2014

Related U.S. Application Data

(60) Provisional application No. 61/784,110, filed on Mar. 14, 2013.

(51) Int. Cl.
*A61N 5/10* (2006.01)

(52) U.S. Cl.
CPC ......... *A61N 5/1001* (2013.01); *A61N 5/1031* (2013.01); *A61N 5/1038* (2013.01); *A61N 5/1047* (2013.01); *A61N 5/1048* (2013.01); *A61N 5/1064* (2013.01)

(58) Field of Classification Search
CPC .... A61N 5/1001; A61N 5/1007; A61N 5/103; A61N 5/1031; A61N 5/1037; A61N 5/1038; A61N 2005/1032; A61N 2005/1034; A61N 5/1014–1016; A61N 5/1027; A61N 2005/1035

See application file for complete search history.

(56) References Cited

U.S. PATENT DOCUMENTS

| | | | |
|---|---|---|---|
| 2006/0274885 A1 | 12/2006 | Wang | |
| 2008/0242914 A1* | 10/2008 | Henderson | A61N 5/103 600/1 |
| 2009/0161826 A1* | 6/2009 | Gertner | A61N 5/1017 378/65 |
| 2009/0182187 A1* | 7/2009 | Chaswal | A61N 5/1031 600/3 |
| 2010/0322381 A1 | 12/2010 | Stahl | |
| 2012/0136194 A1 | 5/2012 | Zhang | |

OTHER PUBLICATIONS

Trnková, Petra et al.; "New Inverse Planning Technology for Image-Guided Cervical Cancer Brachytherapy: Description and Evaluation Within a Clinical Frame," Radiotherapy and Oncology 93 (2009) pp. 331-340.

* cited by examiner

*Primary Examiner* — Carrie R Dorna
(74) *Attorney, Agent, or Firm* — Fitch, Even, Tabin & Flannery LLP

(57) ABSTRACT

A control circuit optimizes a brachytherapy radiation treatment plan for a patient target volume by defining a radiation-control structure that conformally surrounds the patient target volume and then automatically removes part, but not all, of the radiation-control structure to control consideration of radiation sources that are not disposed within the patient target volume. By one approach the control circuit selectively removes parts of the radiation-control structure as a function of the geometry as corresponds to placement of one or more of the radiation sources. For many application settings it serves well for the radiation-control structure to represent a radiation-avoidance area.

8 Claims, 2 Drawing Sheets

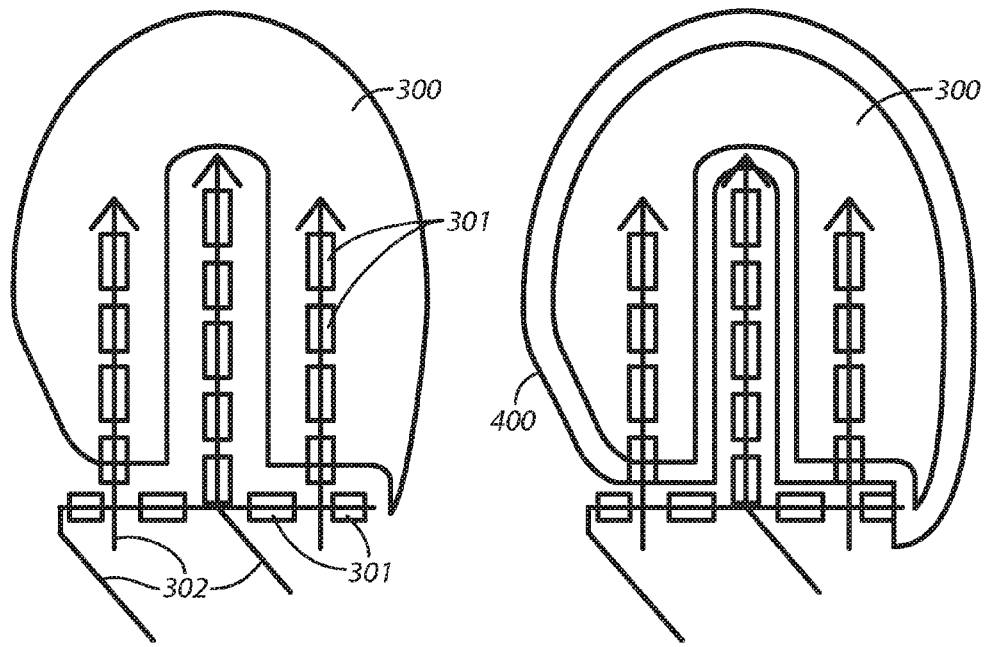
FIG. 3      FIG. 4
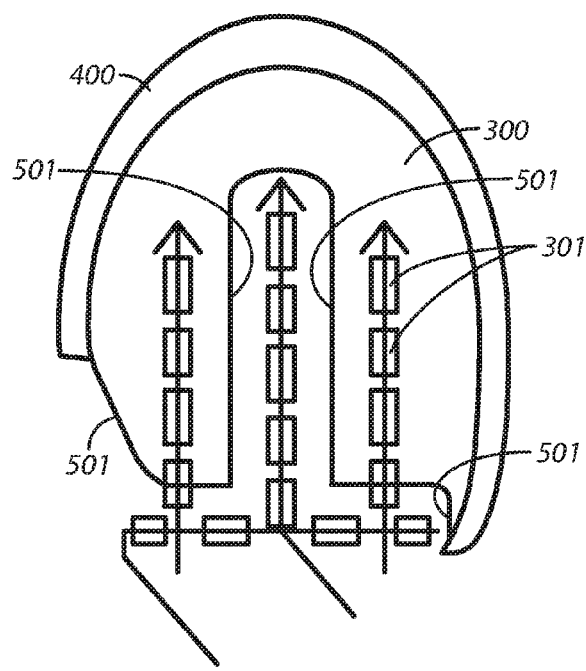
FIG. 5

METHOD FOR OPTIMIZING A BRACHYTHERAPY RADIATION TREATMENT PLAN

RELATED APPLICATION(S)

This application claims the benefit of U.S. Provisional application No. 61/784,110, filed Mar. 14, 2013, which is incorporated by reference in its entirety herein.

TECHNICAL FIELD

This invention relates generally to the therapeutic irradiation of a patient's target volume and more particularly to brachytherapy.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Brachytherapy a form of radiotherapy where one or more radiation sources are placed inside or next to the patient's target volume. The radiation sources are typically precisely placed (often using applicators through which the radiation sources can be moved) and are usually removed after completing a predetermined period of exposure (often referred to as dwell time).

A brachytherapy treatment plan for a specific patient will typically specify such things as the number of radiation sources, their strength(s), their placement, and their dwell time. Such treatment plans are often optimized (in whole or in part) prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using one or more automatically-modified (i.e., "incremented") treatment plan optimization parameters (such as, for example, dwell time).

Such radiation sources are often placed within the patient's target volume but such is not always the case. Sometimes a treatment plan can best serve the overall objectives of the therapy if one or more radiation sources are positioned outside the patient volume. Such is often the case, for example, with ring and tandem applicators, vaginal cylinders, and surface applicators. For a variety of reasons, however, optimization techniques can be less successful when considering radiation sources that are not limited to placement within the target volume.

BRIEF DESCRIPTION OF THE DRAWINGS

The above needs are at least partially met through provision of the apparatus and method for optimizing a brachytherapy radiation treatment plan described in the following detailed description, particularly when studied in conjunction with the drawings, wherein:

FIG. 3 comprises a schematic representation as configured in accordance with various embodiments of the invention;

FIG. 4 comprises a schematic representation as configured in accordance with various embodiments of the invention; and FIG. 5 comprises a schematic representation as configured in accordance with various embodiments of the invention.

Figure 1:
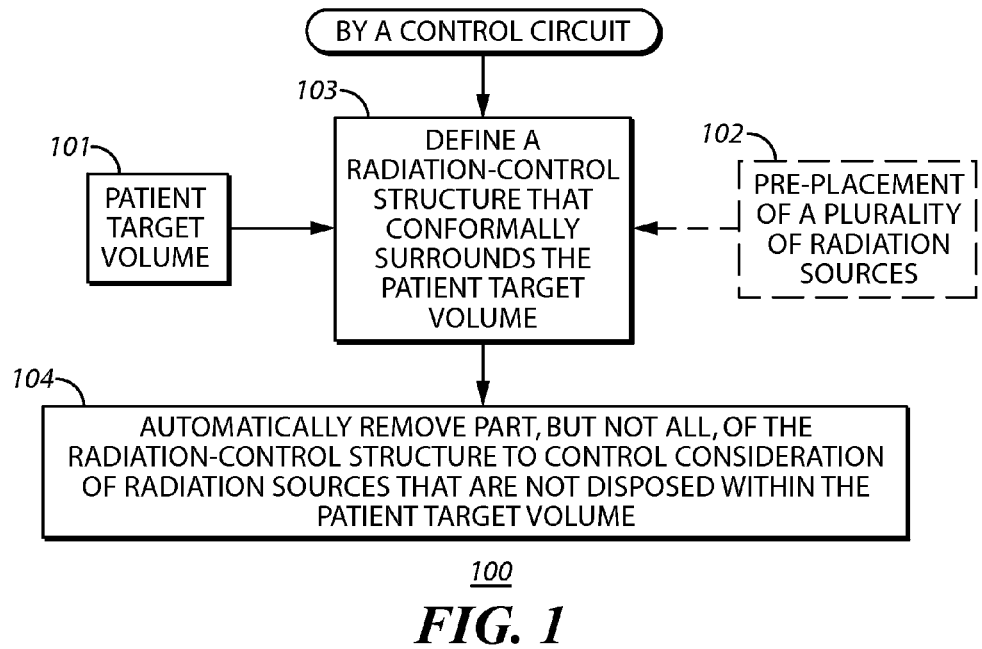
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit optimizes a brachytherapy radiation treatment plan for a patient target volume by defining a radiation-control structure that conformally surrounds the patient target volume and then automatically removes part, but not all, of the radiation-control structure to control consideration of radiation sources that are not disposed within the patient target volume. By one approach the control circuit selectively removes parts of the radiation-control structure as a function of the geometry as corresponds to placement of one or more of the radiation sources. For many application settings it serves well for the radiation-control structure to represent a radiation-avoidance area.

These teachings will accommodate use both with radiation treatment plans that presume static pre-placement of the radiation sources and radiation treatment plans that permit revising placement of the radiation sources during the optimization process. In any event these teachings will accommodate a wide range of optimization parameters including, for example, the number of radiation-source applicators and/or the placement of such applicators, placement of one or more radiation sources, radiation-source strength, and dwell time for radiation source irradiation exposure, to note but a few examples in these regards.

So configured, the radiation-control structure serves well during optimization to constrain, in a useful way, exposure of non-targeted volumes to radiation. At the same time, the selective removal of portions of the radiation-control surface offers a way to permit the optimization process to make therapeutically-beneficial use of radiation sources that are positioned external to that target volume.

These teachings are highly flexible in practice and will readily accommodate modifications and variations as desired. As one example in these regards, smoothing techniques can be applied following the removal of one or more parts of the radiation-control structure. As another example in these regards, small non-contiguous removed areas from the radiation-control structure can be reinstated to reduce computational complexities during optimization that will likely serve no particularly useful purpose.

These and other benefits may become clearer upon making a thorough review and study of the following detailed description. Referring now to the drawings, and in particular to FIG. 1, an illustrative process 100 that is compatible with many of these teachings will now be presented. For the sake of an illustrative example it will be presumed here that a control circuit of choice carries out this process 100.

Figure 2:
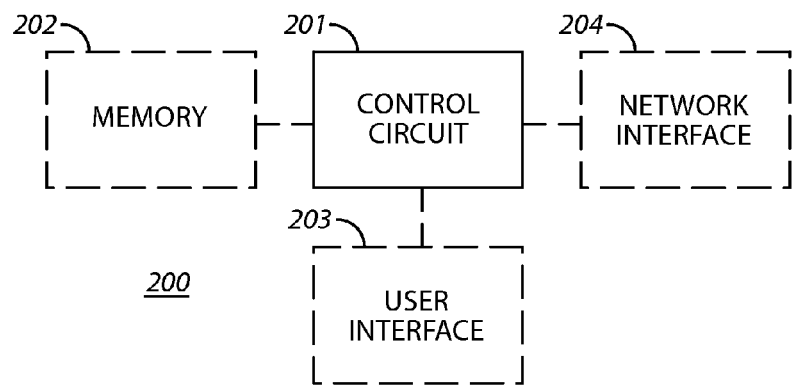
FIG. 2 comprises a block diagram as configured in accordance with various embodiments of the invention.

With momentary reference to FIG. 2, this control circuit 201 can comprise a part of an enabling apparatus 200 that may also include a memory 202 and an optional user interface 203 that both operably couple to the control circuit 201. Such a control circuit 201 can comprise a fixed-purpose hard-wired platform or can comprise a partially or wholly programmable platform. These architectural options are well known and understood in the art and require no further description here. This control circuit 201 is configured (for example, by using corresponding programming as will be well understood by those skilled in the art) to carry out one or more of the steps, actions, and/or functions described herein.

The memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

This memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The user interface 203 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

The control circuit 201 can also optionally operably couple, if desired, to one or more network interfaces 204 including both wireless and non-wireless interfaces as desired. Such a network interface 204 can serve, for example, to communicatively couple the control circuit 201 to one or more local data/communications networks and/or wide area networks (such as, but not limited to, the Internet) as desired. So configured, the control circuit 201 can, for example, receive some or all of the information described herein and/or can communicate its results via the network interface(s) 204.

Referring again to FIG. 1, this process 100 provides, at block 101, information regarding a patient target volume. Various approaches are known in the art to collect and render such information including, by way of example, X-ray computed tomography. For many application settings it will suffice for the information to comprise one or more images (such as a two-dimensional rendering of a three-dimensional volume) of the patient's target volume. As a simple illustrative example in these regards, FIG. 3 depicts such an image that comprises a view where the patient treatment volume 300 corresponds to the patient's cervix. Providing such information regarding a contoured patient target volume comprises a very well understood area of prior art endeavor that requires no further elaboration here.

By one approach the control circuit 200 may also have access to pre-placement information 102 regarding a plurality of radiation sources with respect to the patient target volume 300. FIG. 3 illustrates the pre-placement of both a plurality of radiation sources (schematically represented as small rectangles, some of which are denoted by reference numeral 301) and corresponding applicators (represented as straight lines, some of which are denoted by reference numeral 302).

For the sake of simplicity it is presumed here that the applicators 302 and radiation sources 301 are statically pre-placed and that the optimization process will not address modifying those aspects of the treatment field. It will be understood, however, that the present teachings are not so limited. Instead, these teachings can readily accommodate pre-placing only some applicators 302 and/or radiation sources 301 (or none) and leaving it to the optimization process to at least suggest possibilities in these regards. These teachings will also accommodate permitting the optimization process to dynamically modify the location of radiation sources 301 and/or the location of one or more applicators if desired.

At block 103 this process 100 then provides for defining a radiation-control structure that conformally surrounds the patient target volume 300. Continuing with the example begun in FIG. 3, FIG. 4 illustrates such a radiation-control structure 400. By one approach this radiation-control structure 400 comprises a radiation-avoidance area and hence an area that the optimizer should avoid as much as possible while ensuring appropriate irradiation of targeted volumes. Generally speaking, then, the radiation-control structure 400 reflects a presumption that everything outside the patient target volume 300 is normal tissue that should be avoided.

In this illustrative example of FIG. 4 the radiation-control structure 400 completely surrounds the three-dimensional volume of the patient target volume 300. Also in this illustrative example the radiation-control structure 400 has a thickness (such as, for example, 1 mm, 2 mm's, 5 mm's, or some other thickness of choice). By one approach the radiation-control structure 400 uniformly presents a radiation-avoidance preference. In other words, the optimizer will "see" a region where radiation is to be avoided everywhere within the body with a same degree of preference.

By another approach, if desired, the radiation-control structure 400 can present non-uniform radiation-avoidance preferences. As one example in these regards the radiation-control structure 400 can present a gradient of avoidance preferences such that the preference for avoiding radiation increases (linearly or otherwise as desired) with distance from the patient target volume 300. Such an approach can provide an optimizer with greater latitude with respect to permitting some amount of radiation in areas outside the patient treatment volume while still tending to discourage radiation in such non-targeted areas.

At block 104 the process 100 then provides for automatically removing part, but not all, of the radiation-control structure 400 to control consideration of radiation sources that are not disposed within the patient target volume 300. FIG. 5 provides an illustrative example in these regards that continues from the example of FIGS. 3 and 4. In this illustrative example the radiation-control structure 400 has been removed from areas of the patient target volume 300 that is generally denoted by reference numeral 501.

By one approach, the control circuit 201 manages this selective partial removal of the radiation-control structure 400 as a function, at least in part, of the geometry that corresponds to placement of at least one some of the plurality of radiation sources. For example, by one approach the control circuit 201 develops a ray trace from each voxel within the radiation-control structure 400 to the locations of the radiation sources 301 that are positioned outside the patient target volume 300. The foregoing can be accomplished, for example, using the ray picking algorithm described in *Essential Mathematics for Games & Interactive Applications A Programmer's Guide*, Ch 5.6 Picking/Van Verth, Bishop/Elsevier 2004/ISBN: 1-55860-863-X (the entire contents of which are fully incorporated herein by this reference). The control circuit 201 can then remove all radiation-control structure 400 volume where direct line of sight from normal tissue voxels to any of the selected source positions exists.

In some application settings it can be useful to exclude distant (to the voxel in question) external source positions from the aforementioned ray tracing. Including such positions can result in the unnecessary removal of radiation-control structure 400 where distant external source positions would not actually contribute a meaningful dose to the target region compared to more proximal external source positions. This circumstance arises because point source dose rate attenuation is in inverse square relation to the distance. Excessive radiation-control structure 400 removal has the potential to unduly impair dose control from source positions inside the patient target volume 300.

There can be different criteria for selecting source positions for ray-tracings to localize the removal effect to only the most significant source positions. A distance threshold, for example, might select only source positions that are within a certain specified predetermined distance from the voxel point under consideration. A relative distance threshold, as another example, might select only the points within a certain distance relative to the distance to a nearest source position (for example, all source positions within 1.5 times the distance to the nearest source position).

It can also be useful to limit the effect of radiation-control structure 400 removal along such rays, even in cases where the source position itself is the nearest one outside the patient target volume 300. There may be source positions inside the patient target volume 300, for example, that are much closer to the target volume region near the radiation-control structure voxel under examination that already adequately irradiate the target region. In such a case, removing the radiation-control structure 400 in such a region might permit excessive dosing to normal tissue from the internal source positions.

By way of an illustrative example and without intending any particular limitations in these regards, one approach to determine removal distance along such a ray can comprise finding the distance to its nearest source position for each voxel of target volume and then choosing a maximum of these distances (Dmax) to use to limit removal of the radiation-control structure 400. This distance is the maximum distance between any voxel to be irradiated and the source position that will predominantly irradiate that particular voxel. For many application settings no external target volume source position needs to irradiate voxels farther away than this distance.

By one approach the control circuit 201 can omit ray-tracing when the distance between a radiation-control structure 400 voxel and a given source position is longer than the aforementioned Dmax threshold.

As suggested above, these activities can comprise (in whole or in part) a part of an optimization process. For example, the aforementioned control of considering radiation sources 301 that are not disposed within the patient target volume 300 can occur when optimizing a brachytherapy radiation treatment plan for the patient target volume 300 with respect to any of a variety of optimization parameters (including but not limited to the number of radiation-source applicators 302, placement of at least one radiation-source applicator 302, placement of at least one radiation source 301, a radiation-source strength (which may be governed by, for example, size, shape, and/or material constituency of the radiation source 301), and/or dwell time for radiation source irradiation exposure as desired).

By one approach, and as desired, small non-contiguous parts of the radiation-control structure 400 can be removed and/or smoothed to avoid, for example, removal of areas that are too small to be useful from a planning standpoint. Those skilled in the art will recognize "smoothed" as referring to the statistics/image processing-based processing of a given data set to create an approximating function that works to capture significant patterns within the data while not necessarily capturing noise or fine-scale structures and rapid phenomena. Generally speaking, smoothing aims to offer a general idea of relatively slow changes of value with little attention being paid to closely matching the data values per se. Smoothing methodologies typically have one or more associated tuning parameters that serve to control the extent of the smoothing.

Those skilled in the art will recognize that when brachytherapy is applied external to a target volume (such as a tumor) through a body cavity (or via a ring and tandem applicator as mentioned earlier), the applicator, although indeed external to the target volume, can still be in direct contact with the target volume. In such a case, from the direction of the source position there is typically no healthy tissue between the target volume and the external source position. Instead there is only air and/or the applicator material. Such a circumstance offers another basis to remove the radiation-control structure from such a direction and this, too, is illustrated in FIGS. 3 through 5 discussed above.

So configured, these teachings provide for creating a unique structure that can be used to constraint brachytherapy treatment plan optimization to thereby spare surrounding healthy tissue while still allowing optimal loading patterns in the applicators.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

As but one example in these regards, the aforementioned pre-placement information can assume any of a variety of forms depending upon the particular instantiation of these teachings. For example, that pre-placement information might itself be derived, at least in part, but initially employing the disclosed control structure approach. For example, a pre-placement plan can be generated as a function of seeking to ensure that the radiation-control structure is as large as possible.

As another example in these regards, the aforementioned concept of configuring the radiation-control structure as a gradient can be leveraged in other and various ways. For example, when employing a gradient and when one would actually begin to remove the radiation-control structure, one can instead determine a weight of avoidance preference. This weight could be, for example, 0% close to the source position (essentially to trigger the need for radiation-control structure removal). The weight can then increase linearly or otherwise until a point is reached where one would actually stop removing the radiation-control structure. The avoidance preference weight at that location would be 100%. In such a case the radiation-control structure comprises a margin around the patient target volume, but a same effect (and actually a more sophisticated effect) is achieved via the weights for the different pixels/regions inside the radiation-control structure.

And as yet another example in these regards, it will be understood that the radiation-control structure can be entirely conceptual from the user point of view if desired, and hence even invisible. In fact, the radiation-control structure does not have to be anything similar to other real structures or organs. It is also not required that the radiation-control structure follow the same concept or characterization as other real structures. Those skilled in the art will further recognize that the radiation-control structure need not, in fact, appears as any kind of region or structure but can represent instead a construction rule (or rules) or model rather than any particular patient structure or segment.

What is claimed is:

1. A method for optimizing a brachytherapy radiation treatment plan for a patient target volume comprising:
by a control circuit:
defining a radiation-control structure that conformally surrounds the patient target volume and wherein the radiation-control structure is a radiation-avoidance area and hence an area that a brachytherapy radiation treatment plan optimizer should avoid as much as possible and wherein the radiation-control structure has a user-chosen thickness;
automatically removing part, but not all, of the radiation-control structure to thereby leave only a remaining part of the radiation-control structure to control consideration of radiation source locations that are not disposed within the patient target volume; and
optimizing the brachytherapy radiation treatment plan for the patient target volume with respect to at least one of the radiation source locations that is not disposed within the patient target volume as a function, at least in part, of the remaining part of the radiation-control structure; and placing radiation sources in a patient with respect to the patient target volume in accordance with the optimized brachytherapy radiation treatment plan.

2. The method of claim 1 wherein the brachytherapy radiation treatment plan presumes pre-placement of a plurality of radiation source locations with respect to the patient target volume.

3. The method of claim 2 wherein automatically removing part, but not all, of the radiation-control structure comprises automatically removing part, but not all, of the radiation-control structure as a function, at least in part, of geometry as corresponds to placement of at least some of the plurality of radiation sources.

4. The method of claim 1 wherein the radiation-avoidance area presents non-uniform radiation-avoidance preferences.

5. The method of claim 4 wherein the non-uniform radiation-avoidance preferences comprise a gradient of radiation-avoidance preferences.

6. The method of claim 1 wherein controlling consideration of the radiation source locations that are not disposed within the patient target volume comprises controlling consideration of the radiation source locations that are not disposed within the patient target volume when optimizing the brachytherapy radiation treatment plan for the patient target volume.

7. The method of claim 6 wherein optimizing the brachytherapy radiation treatment plan for the patient target volume comprises optimizing the brachytherapy radiation treatment plan for the patient target volume with respect to at least one of:
a number of radiation-source applicators;
placement of at least one radiation-source applicators;
placement of at least one of the radiation source locations;
a radiation-source strength;
dwell time for radiation source irradiation exposure.

8. A method comprising:
by a control circuit configured to optimize a brachytherapy radiation treatment plan for a patient target volume:
defining a radiation-control structure that conformally surrounds the patient target volume and wherein the radiation-control structure is a radiation-avoidance area and hence an area that a brachytherapy radiation treatment plan optimizer should avoid as much as possible;
automatically removing part, but not all, of the radiation-control structure to thereby leave only a remaining part of the radiation-control structure to control consideration of radiation source locations that are not disposed within the patient target volume; and
optimizing the brachytherapy radiation treatment plan for the patient target volume with respect to at least one of the radiation source locations that is not disposed within the patient target volume as a function, at least in part, of the remaining part of the radiation-control structure; and
placing radiation sources in a patient with respect to the patient target volume in accordance with the optimized brachytherapy radiation treatment plan.

* * * * *